United States Patent [19]

Lutz et al.

[11] 4,430,114

[45] Feb. 7, 1984

[54] 2,6-DINITROANILINE HERBICIDES, AND USE THEREOF

[75] Inventors: Albert W. Lutz, Princeton; Robert E. Diehl, Lawrenceville, both of N.J.

[73] Assignee: American Cyanamid Company, Stamford, Conn.

[21] Appl. No.: 260,490

[22] Filed: May 4, 1981

Related U.S. Application Data

[62] Division of Ser. No. 60,532, Jul. 25, 1979, Pat. No. 4,288,385.

[51] Int. Cl.$^3$ .................... A01N 37/34; C07C 121/52
[52] U.S. Cl. .................... 71/105; 71/106; 71/109; 71/116; 71/118; 71/121; 260/454; 260/465 E; 560/105; 560/228; 560/250; 562/437; 564/166; 564/253; 564/441
[58] Field of Search .......................... 71/105

[56] References Cited

U.S. PATENT DOCUMENTS

| | | | |
|---|---|---|---|
| 3,886,283 | 5/1975 | Dóry et al. | 71/105 |
| 3,892,555 | 7/1975 | Pass et al. | 71/105 |
| 3,904,667 | 9/1975 | Martin | 71/105 |
| 3,910,783 | 10/1975 | Hunter et al. | 71/105 |
| 3,920,742 | 11/1975 | Lutz et al. | 71/105 |
| 3,979,453 | 9/1976 | Yahner | 71/105 |
| 3,989,508 | 11/1976 | Fisher | 71/105 |
| 4,098,812 | 7/1978 | Lutz et al. | 71/105 |
| 4,251,264 | 2/1981 | Lutz et al. | 71/105 |
| 4,288,385 | 9/1981 | Lutz et al. | 71/105 |
| 4,323,388 | 4/1982 | Pissiotas et al. | 71/105 |

*Primary Examiner*—Donald G. Daus
*Assistant Examiner*—James H. Turnipseed
*Attorney, Agent, or Firm*—H. G. Jackson

[57] ABSTRACT

The invention is preemergence herbicidal methods employing novel dinitroanilines for control of certain grasses and broadleaf weeds in the presence of graminaceous crops, especially rice.

1 Claim, No Drawings

2,6-DINITROANILINE HERBICIDES, AND USE THEREOF

This is a division, of application Ser. No. 060,532, filed July 25, 1979, now U.S. Pat. No. 4,288,385 (1981).

SUMMARY OF THE INVENTION

The present invention relates to certain novel substituted 2,6-dinitroaniline compounds. It further relates to certain novel preemergence and postemergence herbicidal methods employing said substituted 2,6-dinitroanilines.

The novel dinitroaniline compounds of the present invention may be graphically illustrated and defined by formula (I) below:

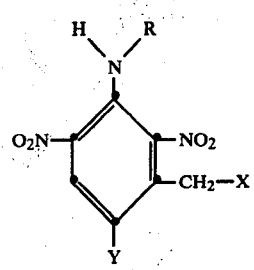

wherein R is secondary alkyl $C_3$-$C_7$ free from quaternary carbon atoms optionally monosubstituted with $OCH_3$ or Cl; X is selected from the group consisting of CN, SCN, OH,

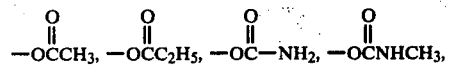

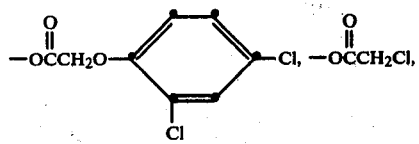

—COOH, —CHO, —CH=NOH, Cl AND Br; Y is selected from the group consisting of $CH_3$, $C_2H_5$, $C_3H_7$-n, $C_3H_7$-i.

A preferred group of compounds represented by formula (I) above are those, wherein X is CN; R and Y are as hereinabove defined.

A more preferred group of compounds of formula (I) are those, wherein X is CN; R is —$CH(C_2H_5)_2$; Y is —$CH_3$, —$C_2H_5$ or —$CH(CH_3)_2$.

The herbicidal compounds of the present invention may be prepared by methods known in the art as hereinbelow described.

Formula (I) compounds, wherein X is $OR_1$ and $R_1$ is the radical of a carboxylic acid such as acetyl, propionyl, (2,4-dichlorophenoxy)acetyl; and the like, can be conveniently prepared from the corresponding alcohol (II), as illustrated below:

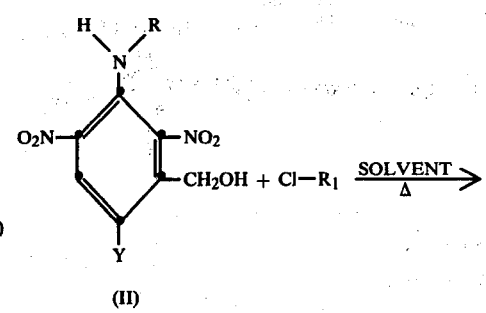

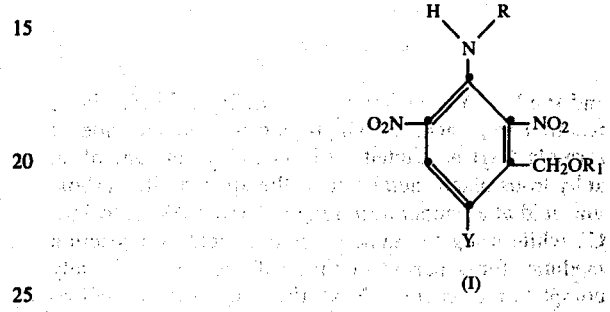

wherein R and Y are as hereinabove defined, and $R_1$ is selected from

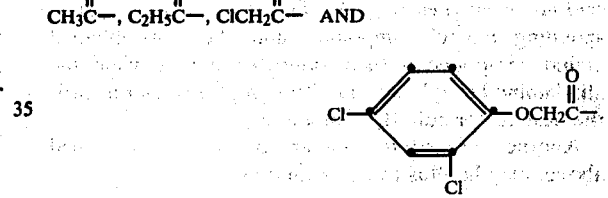

Thus, the alcohol (II) and acid chloride Cl-$R_1$ are dissolved in an inert, anhydrous, solvent such as benzene, toluene or xylene, and the solution heated to about 50° C. to 80° C. until the reaction is essentially complete. Equally good results are obtained if the alcohol (II) is reacted with the appropriate acid anhydride under conditions similar to those described above.

Another method of preparation may be illustrated as follows:

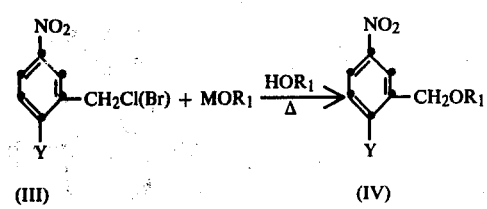

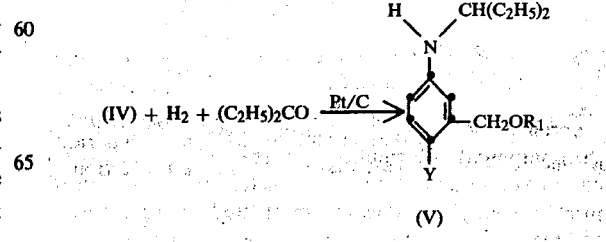

-continued (V) + [H₂O + H₂SO₄ + HNO₃] ⟶ 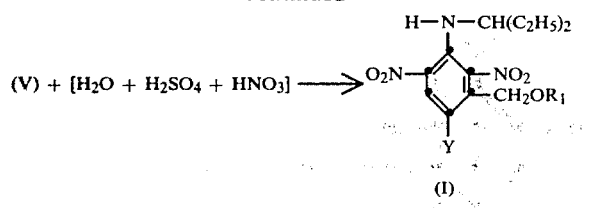

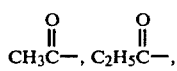

(I)

wherein M is an alkali metal selected from sodium, potassium and lithium; R₁ is selected from $$\underset{CH_3\overset{O}{\underset{\|}{C}}-,\ C_2H_5\overset{O}{\underset{\|}{C}}-,}{}$$

and the like; Y is as hereinabove defined. In the above reaction sequence, a 2-alkyl-5-nitrobenzyl chloride of formula (III) is reacted with an excess amount of an anhydrous alkali metal salt of the appropriate carboxylic acid at a temperature range of about 80° C. to 110° C., while using the same carboxylic acid as a reaction medium, for a period of time sufficient to essentially complete the reaction. Next, the thus-obtained 2-alkyl-5-nitrobenzyl ester of formula (IV) is reductively alkylated using hydrogen and a Pt/C catalyst and diethyl ketone as reactant-solvent. Finally, the alkylamino benzyl ester of formula (V) is dinitrated in a mixed acid to afford the desired formula (I) compound. Alternatively, said nitrobenzyl ester (IV) is first reduced to the corresponding amino compound, and the thus-obtained amino compound is then monoalkylated to yield the alkylamino benzyl ester. Dinitration of this ester affords the desired formula (I) compound.

Another procedure, similar to the one described above, may be illustrated as follows:

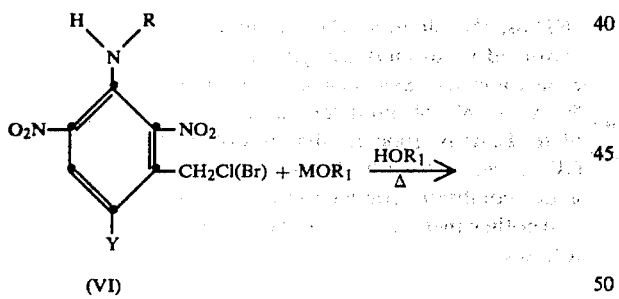

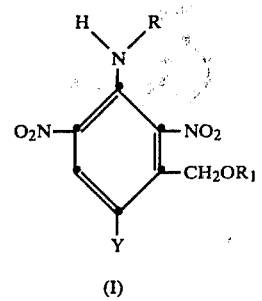

(I)

wherein M, R, R₁ and Y are as hereinabove defined, and the compound of formula (VI) is reacted with an excess amount of an anhydrous alkali metal salt of the appropriate carboxylic acid as a reaction medium, for a period of time sufficient to essentially complete the reaction.

Formula (I) compounds, wherein X is cyano, may be prepared by a reaction sequence illustrated and discussed in detail as follows:

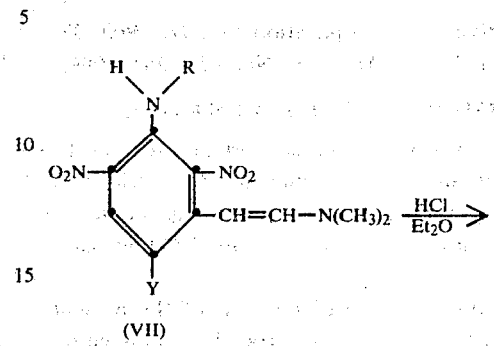

(VII)

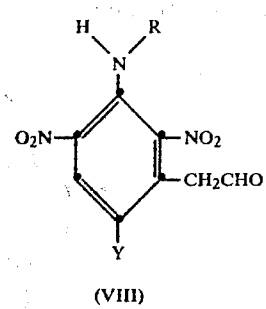

(VIII)

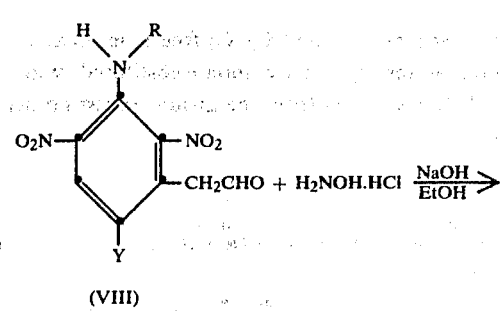

(VIII)

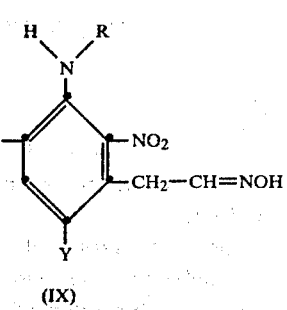

(IX)

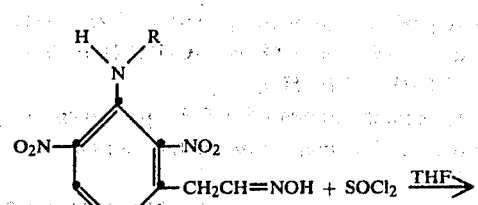

(IX)

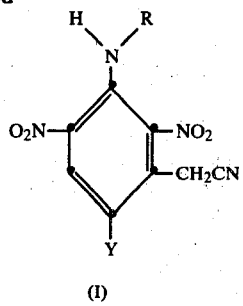

(I)

wherein R and Y are as hereinabove defined. Thus, a styrylamine of formula (VII) is hydrolyzed with an aqueous acid, such as hydrochloric acid, to the corresponding aldehyde (VIII), preferably in the presence of a water-immiscible solvent, such as ether. The aldehyde (VIII) is isolated from the ethereal solution and is then reacted with hydroxylamine in the presence of a lower alcohol, such as ethanol, and an aqueous base, such as sodium hydroxide, to yield the oxime of formula (IX), wherein the hydroxylamine is generated in situ from its hydrochloride salt with an excess amount of said base. Finally, the oxime (IX) is reacted with excess thionyl chloride in the presence of tetrahydrofuran (THF) to afford the desired formula (I) cyano compound.

In general, as stated above, the compounds represented and defined by formula (I) above can be prepared by known methods and procedures, as illustrated and exemplified hereinbelow.

The preemergence herbicidal compositions of the present invention are solid or liquid formulations comprising an effective amount of one or more of the compounds of formula (I) with a herbicidal adjuvant; i.e., an inert carrier, or other conventional formulation aid.

Preparation of said compositions broadly involves admixing an effective amount of the herbicidal agent and adjuvant.

Use of said compositions broadly involves application of an effective amount of said compounds, preferably admixed with an adjuvant to the soil containing seeds or seedlings of the plants to be controlled. Applied in this fashion, the compounds of the present invention selectively control certain mono- and dicotyledonous plants in the presence of graminaceous crops, especially rice.

Interestingly enough, compounds of the present invention, when applied postemergence, selectively control crabgrass and certain broadleaved weeds in the presence of established turf grasses.

Typical formulations include, for example, dusts, dust concentrates, wettable powders, flowable compositions, granulars, emulsifiable concentrates, and the like. Application by conventional methods and equipment is usually made at rates of from about 0.03 kg per hectare to about 11 kg per hectare, and preferably 0.1 kg to 2.0 kg per hectare of active material.

Dusts are generally prepared by grinding together from about 1% to 15% by weight of the active material with from about 99% to 85% by weight of a solid diluent, such as an attaclay, kaolin, diatomaceous earth, fullers earth, talc, pumice, or the like.

Dust concentrates are prepared in similar fashion to the dusts, excepting that generally about 15% to about 95% by weight of active material is used.

Granular formulations may be prepared by applying a liquid solution of the active material to sorptive granular carriers, such as attaclay, kaolin or diatomite granules. Alternatively, they may be mixed with inert carriers and applied to non-sorptive granules, such as sand or limestone.

Typically, a wettable powder can be prepared by grinding together about 25% to 80% by weight of a formula (I) compound, about 2% to 5% by weight of a surfactant such as sodium N-methyl-N-oleoyl taurate, alkyl phenoxy polyoxyethylene ethanol, or sodium alkyl naphthalene sulfonate, 5% to 10% by weight of a dispersing agent, such as a highly purified sodium lignosulfonate, and 25% to 63% by weight of a finely divided carrier, such as kaolin, attapulgite, diatomaceous earth, or the like.

Flowable concentrates can be prepared by grinding together about 40% to 60% by weight of a formula (I) compound, 2% to 3% by weight of the sodium salt of condensed naphthalene sulfonic acids, 2% to 3% by weight of a gelling clay, 2% by weight of propylene glycol, and from 54% to 32% by weight of water.

Emulsion concentrates are prepared by dissolving 15% to 70% by weight of the compound in 85% to 30% by weight of a solvent, such as benzene, toluene, xylene, kerosene, formamide, methylformamide, and the like. Advantageously, surfactants, such as polyoxyethylated vegetable oil or an alkyl phenoxy polyoxyethylene ethanol, are also incorporated in amounts of 1% to 5% by weight of said concentrate.

In using wettable powders, emulsion concentrates, and the like, the formulated material is generally dispersed in water and applied at a rate of from about 0.03 kg per hectare to about 2.0 kg per hectare of active compound to the plants or to the soil containing the seeds of said plants.

The present invention is further illustrated by the following examples which are not to be taken as limitative thereof.

EXAMPLE 1

Preparation of 3-[(1-Ethylpropyl)amino]-6-methyl-2,4-dinitrobenzyl (2,4-dichlorophenoxy)acetate 3-[(1-Ethylpropyl)amino]-6-methyl-2,4-dinitrobenzyl alcohol (2.0 g; 0.007 mol) and 2,4-dichlorophenoxyacetyl chloride (used in excess over theory) are dissolved in benzene, and the solution stirred at 60° C. until tlc (silica gel-benzene) indicates the reaction to be complete. The reaction mixture is then cooled down, diluted with ether, and washed with dilute sodium bicarbonate solution until the washings became alkaline. The organic layer is then separated, dried over magnesium sulfate, and evaporated to afford a liquid residue, which solidifies gradually (3.3 g; 94%). Recrystallization of this solid from methanol affords 1.4 g of title product, melting point 103°–106° C.

Analysis calculated for $C_{21}H_{23}N_3O_7Cl_2$: C, 50.40; H, 4.60; N, 8.40; Cl, 14.20. Found: C, 50.30; H, 4.91; N, 8.27; Cl, 14.29.

EXAMPLE 2

Preparation of {5-[(1-Ethylpropyl)amino]-4,6-dinitrio-o-cumenyl}acetic acid

A mixture of concentrated sulfuric acid (4.25 g) and water (17.3 g) is cooled to about 12° C., and a solution of {5-[(1-ethylpropyl)amino]-4,6-dinitro-o-cumenyl}-acetaldehyde (6.5 g; 0.0192 mol) in methylene chloride (40 ml) is added slowly while the temperature of the mixture is maintained at about 12° C. Next, potassium permanganate (3.0 g; 0.0192 mol) is added in small portions. After stirring overnight at room temperature, tlc indicates the presence of some starting material. The mixture is cooled to 15° C., and a second portion of potassium permanganate (3.0 g; 0.0192 mol) added. When tlc indicates the absence of starting material, sodium thiosulfate is added until a clear red solution is obtained. Methylene chloride is added and the layers are separated. The methylene chloride layer is washed, dried over magnesium sulfate, and evaporated to leave a red oil (6.6 g; 97%) which slowly solidifies to a yellow solid. This solid is purified by column chromatography using 90/10 toluene/ethyl acetate to elute the product, melting point 116°–118° C. An analytical sample, recrystallized from pentane, melts at 117.5°–118.5° C.

Analysis calculated for $C_{16}H_{23}N_3O_6$: C, 54.38; H, 6.56; N, 11.89. Found: C, 54.41; H, 6.60; N, 11.90.

EXAMPLE 3

Preparation of 3-[(1-Ethylpropyl)amino]-6-methyl-2,4-dinitrobenzyl acetate

A solution of 5-[(1-ethylpropyl)amino]-2-methylbenzyl acetate (14.0 g; 0.056 mol) in dichloroethane (140 ml) is treated at 20°–27° C. with a nitrating mixture prepared from water (9.2 g), sulfuric acid (19.6 g) and nitric acid (24.0 g; 0.27 mol). Ninety minutes after the start of the reaction, glc (OV17 on Gas Chrom Q, at 250° C.) indicates that <3% of starting material is present. The reaction mixture is poured into water and extracted with methylene chloride. The organic layer is washed in succession with water, dilute base, saturated brine, and is then dried.

Concentration of the solution in vacuo leaves a dark brown oil (16.3 g; 85%). This oil is dissolved in methanol (50 ml), and the solution inoculated with seed crystals to deposit the title product (6.8 g), an orange solid, melting point 47°–49° C.

Analysis calculated for $C_{15}H_{21}N_3O_6$: C, 53.09; H, 6.24; N, 12.38. Found: C, 53.06; H, 6.32; N, 12.52.

EXAMPLE 4

Preparation of 3-[(1-Ethylpropyl)amino]-6-methyl-2,4-dinitrobenzyl propionate

3-[(1-Ethylpropyl)amino]-6-methyl-2,4-dinitrobenzyl alcohol (1.0 g; 0.0034 mol) and propionic anhydride (0.45 g; 0.003 mol) are dissolved in benzene (10 ml) and the solution stirred for 2 hours with no sign of reaction. One drop of concentrated sulfuric acid is added, and the mixture stirred overnight at room temperature. It is then poured into a mixture of water and ether, and the mixture stirred for 30 minutes. The ether layer is separated, washed in succession with dilute sodium bicarbonate solution and saturated brine and dried. Evaporation of the solution in vacuo leaves 1.2 g (100%) of an orange oil, which is chromatographed on 10 g of silica gel to afford the title product, melting point 27°–29° C.

Analysis calculated for $C_{16}H_{23}N_3O_6$: C, 54.38; H, 6.56; N, 11.89. Found: C, 54.17; H, 6.56; N, 11.68.

EXAMPLE 5

Preparation of 3-[(1-Ethylpropyl)amino]-6-methyl-2,4-dinitrobenzyl alcohol

A sample of 3-[(1-ethylpropyl)amino]-6-methyl-2,4-dinitrobenzyl acetate (23.1 g; 0.068 mol) is added to a mixture of concentrated hydrochloric acid (30 ml), water (40 ml) and methanol (320 ml). The reaction mixture is refluxed for 4 hours, cooled down and concentrated in vacuo. It is then diluted with water, extracted with ether, and the ether layer dried. The ether is removed in vacuo to leave a red oil, which readily solidifies to a yellow-orange solid (19.9 g; 98.5%). A similarly prepared and purified sample has a melting point of 51°–54° C.

Analysis calculated for $C_{13}H_{19}N_3O_5$: C, 52.41; H, 6.44; N, 14.13. Found: C, 52.94; H, 6.40; N, 13.99.

EXAMPLE 6

Preparation of 3-[(1-Ethylpropyl)amino]-6-methyl-2,4-dinitrobenzyl methylcarbamate A mixture of 3-[(1-ethylpropyl)amino]-6-methyl-2,4-dinitrobenzyl alcohol (1.0 g; 0.0033 mol), methyl isocyanate (used in excess over theory), triethylamine (1 drop) and benzene (10 ml) is refluxed for 2 hours. The precipitated solid is collected to afford 1.1 g (91.6%) title product, melting point 117°–120° C.

Analysis calculated for $C_{15}H_{22}N_4O_6$: C, 50.84; H, 6.26; N, 15.81. Found: C, 51.12; H, 6.18; N, 15.74.

EXAMPLE 7

Preparation of 3-[(1-Ethylpropyl)amino]-6-methyl-2,4-dinitrobenzyl chloroacetate A mixture of 3-[(1-ethylpropyl)amino]-6-methyl-2,4-dinitrobenzyl alcohol (1.1 g; 0.0037 mol), chloroacetic anhydride (0.64 g; 0.0037 mol), sulfuric acid (1 drop) and benzene (10 ml) is stirred for 24 hours at room temperature. Tlc indicates incomplete reaction; therefore, additional chloroacetic anhydride (0.1 g; 0.0005 mol) is added and stirring continued for 24 hours. Next, water is added, the mixture stirred for 0.5 hour, and the layers separated. The organic layer is diluted with ether, washed with dilute potassium carbonate solution, dried and evaporated to leave an oil (1.2 g; 86.8%), which readily solidifies, melting point 45°–48° C.

Analysis calculated for $C_{15}H_{20}N_3O_6Cl$: C, 48.19; H, 5.35; N, 11.24. Found: C, 48.35; H, 5.51; N, 11.23.

EXAMPLE 8

Preparation of {5-[(1-Ethylpropyl)amino]-4,6-dinitro-o-tolyl}acetonitrile

A solution of thionyl chloride (25.0 ml) in tetrahydrofuran (THF; 100 ml) is added at <20° C. to a solution of {5-[(1-ethylpropyl)amino]-4,6-dinitro-o-tolyl}acetaldehyde oxime (12.0 g; 0.037 mol) in THF (160 ml). The reaction mixture is stirred overnight at room temperature, filtered, and the filtrate concentrated in vacuo to leave an oil which crystallizes, when seeded, to afford the title product (9.8 g), an orange solid. A sample is purified for analysis, melting point 59°–60° C.

Analysis calculated for $C_{14}H_{18}N_4O_4$: C, 54.89; H, 5.92; N, 18.29. Found: C, 55.11; H, 5.70; N, 18.48.

By the above procedure, the following additional nitriles are made:

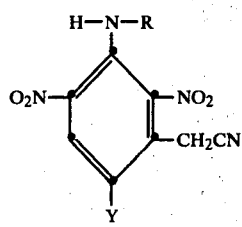

| R | Y | Melting Point °C. |
|---|---|---|
| —CH(C₂H₅)₂ | —CH(CH₃)₂ | 65–66.5 |
| —CH(CH₃)C₂H₅ | —CH₃ | 80–82 |
| —CH(CH₃)CH₂OCH₃ | —CH₃ | 71–73 |
| —CH(CH₃)C₃H₇—n | —CH₃ | red oil |
| —CH(CH₂OH)C₂H₅ | —CH₃ | 82–84 |
| —C₃H₇—n | —CH₃ | 89–91 |
| —CH(C₂H₅)C₃H₇—n | —CH₃ | red oil* |
| —CH(C₂H₅)CH₂CH₂Cl | —CH₃ | red oil |
| —CH(CH₃)₂ | —C₃H₇—n | 77–78.5 |

EXAMPLE 9

Preparation of {5-[(1-Ethylpropyl)amino]-4,6-dinitro-o-tolyl}acetamide

A sample of {5-[(1-ethylpropyl)amino]-4,6-dinitro-o-tolyl}acetonitrile (4.25 g; 0.014 mol) is added to warm t-butanol (40°–45° C.; 50 ml) followed by finely powdered potassium hydroxide (9.0 g; 0.16 mol). Additional t-butanol (20 ml) is added, and the reaction mixture heated at the reflux overnight. The reaction mixture is then cooled, diluted with 200 ml salt solution, and filtered to give 2.5 g (55%) of an orange solid, melting point 192°–194° C. A sample is recrystallized from methanol for analysis, melting point 194°–196° C.

Analysis calculated for C₁₄H₂₀N₄O₅: C, 51.84; H, 6.22; N, 17.28. Found: C, 51.76; H, 6.18; N, 17.38.

EXAMPLE 10

Preparation of 3-[(1-Ethylpropyl)amino]-N,N,6-trimethyl-2,4-dinitrostyrylamine

A mixture of N-(1-ethylpropyl)-2,6-dinitro-3,4-xylidine (50.0 g; 0.18 mol) and dimethylformamide dimethyl acetal (125 ml) is stirred at 85° C. overnight. The temperature of the reaction mixture is then raised to 90°–100° C. and methanol distilled off until approximately 12.5 ml methanol is collected. The reaction mixture is then cooled down, poured into hexane (400 ml) and chilled. The crystallized red solid (45.6 g; 75.3%) is collected and air dried. A sample is purified for analysis, melting point 100°–102° C.

Analysis calculated for C₁₆H₂₄N₄O₄: C, 57.13; H, 7.22; N, 16.61. Found: C, 57.13; H, 7.19; L N, 16.66.

Substituting the appropriate intermediate in the above reaction affords 3-[(1-ethylpropyl)amino]-6-isopropyl-N,N-dimethyl-2,4-dinitrostyrylamine, melting point 88°–89.5° C.

EXAMPLE 11

Preparation of {5-[(1-Ethylpropyl)amino]-4,6-dinitro-o-tolyl}acetaldehyde

A mixture of 1 N hydrochloric acid (300 ml) and a solution of 3-[(1-ethylpropyl)amino]-N,N,6-trimethyl-2,4-dinitrostyrylamine (33.0 g; 0.078 mol) in ether (300–350 ml) is stirred at room temperature for 48 hours. The ether layer is then separated, washed with saturated brine, dried over magnesium sulfate, and evaporated in vacuo to afford a dark yellow solid (28.6 g; 94.3%). A sample is purified for analysis, melting point 60°–61° C.

Analysis calculated for C₁₄H₁₉N₃O₅: C, 54.36; H, 6.19; N, 13.59. Found: C, 54.23; H, 6.42; N, 13.63.

Substituting 3-[(1-ethylpropyl)amino]-6-isopropyl-N,N-dimethyl-2,4-dinitrostyrylamine in the above reaction, the corresponding {5-[(1-ethylpropyl)amino]-4,6-dinitro-o-cumenyl}acetaldehyde, an orange oil, is obtained.

Analysis calculated for C₁₆H₂₃N₃O₅: C, 56.95; H, 6.87; N, 12.45. Found: C, 56.92; H, 6.89; N, 12.49.

EXAMPLE 12

Preparation of {5-[(1-Ethylpropyl)amino]-4,6-dinitro-o-tolyl}acetaldehyde oxime

{5-[(1-Ethylpropyl)amino]-4,6-dinitro-o-tolyl}-acetaldehyde (18.4 g; 0.06 mol) is dissolved in ethanol (360 ml) at 45° C. The solution is cooled to 30° C., hydroxylamine hydrochloride (8.4 g; 0.12 mol) and 3 N sodium hydroxide (31.0 ml) are added. The reaction mixture is stirred overnight at room temperature, concentrated and then diluted with water to precipitate 17.5 g (89.9%) of a syn- and anti-isomeric mixture of the title product.

Analysis calculated for C₁₄H₂₀N₄O₅: C, 51.85; H, 6.22; N, 17.27. Found: C, 51.66; H, 5.95; N, 17.23.

Substituting {5-[(1-ethylpropyl)amino]-4,6-dinitro-o-cumenyl}-acetaldehyde in the above reaction, the corresponding {5-[(1-ethylpropyl)amino]-4,6-dinitro-o-cumenyl}acetaldehyde oxime, melting point 113.5°–115° C., is obtained.

EXAMPLE 13

Preparation of 2-Methyl-5-nitrobenzyl acetate

A slurry of anhydrous sodium acetate (60.0 g; 0.73 mol) in acetic acid (400 ml) is stirred and 2-methyl-5-nitrobenzyl chloride (45.3 g; 0.24 mol) added. The resulting reaction mixture is heated to reflux and is heated overnight at 115° C., after which time tlc (silica gel; 75/25 hexane/benzene) indicates that no starting material is present. The mixture is cooled down, concentrated in vacuo, and diluted with water. The precipitated solid (48.9 g; 95.8%) is collected and dried. A sample recrystallized from hexane has a melting point of 52°–53.5° C.

EXAMPLE 14

Preparation of 5-[(1-Ethylpropyl)amino]-2-methylbenzyl acetate

A mixture of 2-methyl-5-nitrobenzyl acetate (25.0 g; 0.12 mol), diethyl ketone (100 ml), β-naphthalene sulfonic acid (1.8 g) and 5% Pt/C catalyst (2.5 g; 62% wet weight) is hydrogenated in a Parr shaking apparatus until the hydrogen uptake ceases. The mixture is cooled down, filtered, and the filtrate concentrated in vacuo. The residue is dissolved in methylene chloride, the solution washed with water, dried over magnesium sulfate, and is evaporated to leave a brown oil (27.7 g; 92.7%). A sample of this oil is distilled (boiling point 120°–122° C. at 0.1 mm) for analysis.

Analysis calculated for $C_{15}H_{23}NO_2$: C, 72.29; H, 9.24; N, 5.62. Found: C, 72.31; H, 9.66; N, 5.23.

EXAMPLE 15

Preparation of 7-Bromo-N-(1-ethylpropyl)-4,6-dinitro-o-cymen-5-amine

A solution of N-(1-ethylpropyl)-7-methoxy-4,6-dinitro-o-cymen-5-amine (33.0 g; 0.1 mol) in methylene chloride (100 ml) is cooled to −30° C. to −40° C., and a solution of borontribromide (25.0 g; 0.1 mol) in methylene chloride (50 ml) added. The dark reaction mixture is stirred for 2 hours at about −30° C. and then allowed to warm up slowly to room temperature. The mixture is stirred for 48 hours, poured on ice and extracted with methylene chloride. Tlc (silica gel; 90/10 toluene/ethyl acetate) indicates the presence of starting material and a rapidly migrating new component. The solution is filtered through a bed of silica gel and then concentrated to yield 25 g of a mixture consisting of starting material and product. Column chromatography of this crude mixture (silica gel; hexane/methylene chloride) yields 4.4 g of starting material and 6.1 g (33.2%) of product, melting point 52°–56° C.

Analysis calculated for $C_{15}H_{22}BrN_3O_4$: C, 46.39; H, 5.67; Br, 20.67; N, 10.82. Found: C, 46.92; H, 5.76; Br, 20.71; N, 11.05.

EXAMPLE 16

Preparation of 3-[(1-Ethylpropyl)amino]-4,6-dinitrobenzyl acetate

A mixture of 7-bromo-N-(1-ethylpropyl)-4,6-dinitro-o-cymen-5-amine (2.0 g; 0.005 mol), sodium acetate (2.0 g; 0.024 mol) and acetic acid (50 ml) is refluxed overnight. The reaction mixture is then concentrated in vacuo to a solid residue, and this residue partitioned between ether and water. The ether layer is separated, washed in succession with dilute potassium carbonate solution, saturated brine, and is then dried over magnesium sulfate. The dry solution is evaporated in vacuo to leave a yellow solid (1.6 g; 88%), melting point 46°–52° C. An analytical sample is prepared by recrystallizing part of the above material from pentane, melting point 53°–55° C.

Analysis calculated for $C_{17}H_{25}N_3O_6$: C, 55.57; H, 6.86; N, 11.44. Found: C, 55.88; H, 7.16; N, 11.41.

EXAMPLE 17

Preparation of 3-[(1-Ethylpropyl)amino]-6-isopropyl-2,4-dinitrobenzyl thiocyanate A solution of potassium thiocyanate (0.3 g; 0.003 mol) in dimethoxyethane (10 ml) is added to a solution of 7-bromo-N-(1-ethylpropyl)-4,6-dinitro-o-cymen-5-amine (1.2 g; 0.003 mol) in dimethoxyethane (40 ml). The reaction mixture is stirred for one hour at room temperature, one hour at 80° C. and is then concentrated in vacuo. The residue is taken up in ether, and the solution washed with water. The ether layer is dried over magnesium sulfate and evaporated to afford an oil, which crystallizes readily to yield 1.3 g (>100%) of crude solid. This solid is recrystallized from pentane (75 ml) to afford 0.7 g of an orange solid, melting point 68°–70° C.

Analysis calculated for $C_{16}H_{22}N_4SO_4$: C, 52.45; H, 6.05; N, 15.29. Found: C, 52.70; H, 6.24; N, 15.35.

EXAMPLE 18

Preemergence Herbicidal Activity

The preemergence herbicidal activity of the compounds of the present invention is exemplified by the following tests, in which the seeds or propagating organs of a variety of monocotyledonous and dicotyledonous plants are separately mixed with potting soil and planted on top of approximately 2.5 cm of soil in separate cups. After planting, the cups are sprayed with the selected aqueous acetone solution containing test compound in sufficient quantity to provide the equivalent of about 0.035 kg to 11.2 kg per hectare of test compound per cup. The treated cups are then placed on greenhouse benches, watered and cared for in accordance with conventional greenhouse procedures. Three to five weeks after treatment, the tests are terminated, and each cup is examined and rated according to the rating system provided below.

The data obtained are to be found in Table I below. It can be clearly seen from said data, that the compounds of the invention, when applied preemergence, selectively control certain grasses and broadleaved weeds in the presence of graminaceous crops, especially rice.

Rating System

| Rating System: | % Control Compared to Check |
|---|---|
| 9 - Complete kill | 100 |
| 8 - Approaching complete kill | 91–99 |
| 7 - Good herbicidal effect | 80–90 |
| 6 - Herbicidal effect | 65–79 |
| 5 - Definite injury | 45–64 |
| 4 - Injury | 30–44 |
| 3 - Moderate effect | 16–29 |
| 2 - Slight effect | 6–15 |
| 1 - Trace effect | 1–5 |
| 0 - No effect | 0 |
| X - No data available | — |

The above rating scale is based upon visual determination of stand, size, vigor, chlorosis, growth malformation and over-all plant appearance as compared with a control.

PLANT ABBREVIATIONS

| Code | Common Name | Scientific Name |
|---|---|---|
| MU | Mustard, Wild | Brassica kaber, (DC) L.c. Wheelr. |
| PI | Pigweed, Redroot | Amaranthus retroflexus, L. |
| MG | Morningglory, Tall | Ipomoea purpurea, (L.) Roth |
| BA | Barnyardgrass | Echinochloa crusgalli, (L.) Beau. |
| CR | Crabgrass, (Hairy) Large | Digitaria sanguinalis, (L.) Scop. |
| FO | Foxtail, Green | Setaria viridis, (L.) Beauv. |
| VL | Velvetleaf | Abutilon theophrasti, Medic. |
| MJ | Millet, Japanese | Echinochloa crusgalli, Cv. Japmi. |
| CN | Corn, Field | Zea mays, L. |
| CO | Cotton | Gossypium hirsutum, L. |

-continued
PLANT ABBREVIATIONS

| Code | Common Name | Scientific Name |
|---|---|---|
| SY | Soybean | *Glycine max,* (L.) Merr. |
| BY | Barley, Steptoe | *Hordeum vulgare,* Cv. Steptoe |
| WH | Wheat, Spring, Era | *Triticum aestivum,* Cv. Era |
| $RI_a$ | Rice, Star Bonnet | *Oryza sativa,* Cv. Star Bonnet |
| $RI_b$ | Rice, Nato | *Oryza sativa,* Cv. Nato |
| $RI_c$ | Rice, Saturn | *Oryza sativa,* Cv. Saturn |

TABLE 1

Preemergence Herbicidal Activity of Compounds of the Invention

| Compound | Rate kg/ha | BA | CR | FO | MJ | MG | MU | PI | SP | VL | BY | CN | CO | RL$_a$ | RL$_b$ | RL$_c$ | SY | WH |
|---|---|---|---|---|---|---|---|---|---|---|---|---|---|---|---|---|---|---|
| N—(1-Ethylpropyl)-α$^3$-methoxy-2,6-dinitro-3,4-xylidine | 2.0 | 9.0 | 9.0 | 9.0 | 9.0 | 7.7 | 9.0 | 8.7 | 8.0 | 8.0 | 1.0 | 2.7 | 5.0 | 2.7 | 1.0 | 0.0 | 4.3 | 2.0 |
|  | 1.0 | 9.0 | 9.0 | 9.0 | 8.8 | 3.2 | 8.8 | 8.2 | 8.2 | 6.8 | 0.0 | 0.6 | 2.6 | 1.2 | 0.0 | 0.0 | 5.6 | 0.2 |
|  | 0.5 | 9.0 | 9.0 | 9.0 | 8.6 | 0.0 | 8.2 | 7.6 | 8.0 | 5.4 | 0.0 | 0.2 | 0.6 | 0.6 | 0.0 | 0.0 | 2.4 | 0.0 |
|  | 0.25 | 8.6 | 9.0 | 7.8 | 7.8 | 0.0 | 5.4 | 6.6 | 7.8 | 3.2 | 0.0 | 0.0 | 0.0 | 0.0 | 0.0 | 0.0 | 0.0 | 0.0 |
|  | 0.125 | 8.2 | 8.8 | 5.0 | 4.2 | 0.0 | 1.2 | 2.8 | 4.8 | 0.6 | 0.0 | 0.0 | 0.0 | 0.0 | 0.0 | 0.0 | 0.0 | 0.0 |
|  | 0.063 | 5.8 | 8.2 | 3.6 | 1.4 | 0.0 | 0.0 | 0.6 | 2.8 | 0.0 | 0.0 | 0.0 | 0.0 | 0.0 | 0.0 | 0.0 | 0.0 | 0.0 |
|  | 0.032 | 3.3 | 4.0 | 1.5 | 0.0 | 0.0 | 0.0 | 0.5 | 1.3 | 0.0 | 0.0 | 0.0 | 0.0 | 0.0 | 0.0 | 0.0 | 0.0 | 0.0 |
| 3-[(1-Ethylpropyl)amino]-6-methyl-2,4-dinitrobenzyl alcohol, acetate | 2.0 | 9.0 | 9.0 | 9.0 | 8.0 | 0.0 | 6.0 | 5.0 | 8.0 | 2.0 | 0.0 | 0.0 | 1.0 | 0.0 | 0.0 | 5.0 | 0.0 | 0.0 |
|  | 1.0 | 8.0 | 9.0 | 8.0 | 7.5 | 0.0 | 1.0 | 2.5 | 3.0 | 0.0 | 0.0 | 0.0 | 0.0 | 0.0 | 0.0 | 0.0 | 3.5 | 0.0 |
|  | 0.5 | 6.0 | 9.0 | 7.0 | 2.5 | 0.0 | 0.0 | 0.0 | 0.0 | 0.0 | 0.0 | 0.0 | 0.0 | 0.0 | 0.0 | 0.0 | 0.0 | 0.0 |
|  | 0.25 | 4.5 | 9.0 | 4.5 | 0.0 | 0.0 | 0.0 | 0.0 | 0.0 | 0.0 | 0.0 | 0.0 | 0.0 | 0.0 | 0.0 | 0.0 | 0.0 | 0.0 |
|  | 0.125 | 3.5 | 6.0 | 1.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| {5-[(1-Ethylpropyl)amino]-4,6-dinitro-o-tolyl}acetaldehyde, oxime | 1.0 | 9.0 | 9.0 | 6.0 | 8.0 | 0.0 | 5.0 | 7.0 | 8.0 | 3.0 | 0.0 | 0.0 | 5.0 | 0.0 | 0.0 | 0.0 | 5.0 | 0.0 |
|  | 0.5 | 7.0 | 9.0 | 3.0 | 0.0 | 0.0 | 3.0 | 3.0 | 3.0 | 0.0 | 0.0 | 0.0 | 0.0 | 0.0 | 0.0 | 0.0 | 0.0 | 0.0 |
|  | 0.25 | 3.0 | 9.0 | 3.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| {5-[(1-Ethylpropyl)amino]-4,6-dinitro-o-tolyl}acetonitrile | 2.0 | 9.0 | 9.0 | 8.7 | 9.0 | 5.0 | 8.3 | 9.0 | 8.3 | 8.0 | 0.0 | 0.0 | 4.3 | 0.0 | 0.0 | 1.5 | 4.0 | 0.6 |
|  | 1.0 | 8.8 | 9.0 | 7.2 | 8.0 | 1.3 | 7.0 | 8.0 | 8.3 | 4.0 | 0.0 | 0.5 | 1.3 | 0.0 | 0.6 | 0.6 | 3.2 | 0.0 |
|  | 0.5 | 8.2 | 9.0 | 5.3 | 6.7 | 0.0 | 5.2 | 6.2 | 7.7 | 1.7 | 0.0 | 0.0 | 1.0 | 0.6 | 0.6 | 0.2 | 2.7 | 0.0 |
|  | 0.25 | 7.0 | 9.0 | 3.2 | 3.3 | 0.0 | 1.3 | 3.8 | 5.3 | 0.2 | 0.0 | 0.0 | 0.6 | 0.5 | 0.0 | 0.0 | 0.3 | 0.0 |
|  | 0.125 | 5.3 | 8.7 | 1.7 | 0.5 | 0.0 | 0.5 | 0.5 | 2.2 | 0.0 | 0.0 | 0.0 | 0.0 | 0.5 | 0.0 | 0.0 | 0.0 | 0.0 |
|  | 0.063 | 3.2 | 6.7 | 0.0 | 0.3 | 0.0 | 0.0 | 0.3 | 0.5 | 0.0 | 0.0 | 0.0 | 0.0 | 0.0 | 0.0 | 0.0 | 0.0 | 0.0 |
| 2-{5-[(1-Ethylpropyl)amino]-4,6-dinitro-o-tolyl}acetamide | 10.0 | 9.0 | 9.0 | 9.0 | X | 8.0 | 2.0 | 8.0 | 8.0 | 8.0 | X | X | X | X | X | X | X | X |
|  | 2.0 | 9.0 | 9.0 | 6.5 | 9.0 | 0.0 | 0.0 | 5.0 | 3.0 | 5.0 | 0.0 | 0.0 | 1.0 | 0.0 | 0.0 | 0.0 | 0.0 | 0.0 |
|  | 1.0 | 8.0 | 9.0 | 5.0 | 4.0 | 0.0 | 0.0 | 4.0 | 3.0 | 1.0 | 0.0 | 0.0 | 0.0 | 2.5 | 0.0 | 0.0 | 0.0 | 0.0 |
|  | 0.5 | 4.5 | 8.0 | 1.5 | 0.0 | 0.0 | 0.0 | 1.5 | 0.0 | 0.0 | 0.0 | 0.0 | 0.0 | 2.5 | 0.0 | 0.0 | 0.0 | 0.0 |
|  | 0.25 | 3.0 | 6.0 | 1.0 | 0.0 | 0.0 | 0.0 | 0.0 | 0.0 | 0.0 | 0.0 | 0.0 | 0.0 | 1.5 | 0.0 | 0.0 | 0.0 | 0.0 |
|  | 0.125 | 3.0 | 6.0 | 1.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 7-Bromo-N—(1-ethylpropyl)-4,6-dinitro-o-cymen-5-amine | 10.0 | 9.0 | 9.0 | 9.0 | X | 8.0 | 8.0 | 8.0 | 8.0 | 8.0 | X | X | X | X | X | X | X | X |
|  | 2.0 | 9.0 | 9.0 | 9.0 | 9.0 | 7.0 | 8.0 | 8.0 | 8.0 | 5.0 | 0.0 | 1.0 | 1.0 | 3.0 | 0.0 | 0.0 | 1.0 | 0.0 |
|  | 1.0 | 5.5 | 9.0 | 7.0 | 3.5 | 0.0 | 1.0 | 6.5 | 7.0 | 1.0 | 0.0 | 0.0 | 0.0 | 0.5 | 0.0 | 0.0 | 0.0 | 0.0 |
|  | 0.5 | 4.0 | 9.0 | 6.0 | 2.5 | 0.0 | 0.0 | 3.0 | 3.0 | 0.0 | 0.0 | 0.0 | 0.0 | 0.0 | 0.0 | 0.0 | 0.0 | 0.0 |
|  | 0.25 | 3.5 | 9.0 | 4.5 | 2.5 | 0.0 | 0.0 | 0.0 | 0.0 | 0.0 | 0.0 | 0.0 | 0.0 | 0.0 | 0.0 | 0.0 | 0.0 | 0.0 |
|  | 0.125 | 1.5 | 8.0 | 2.5 | 0.0 | 0.0 | 0.0 | 0.0 | 0.0 | 0.0 | 0.0 | 0.0 | 0.0 | 0.0 | 0.0 | 0.0 | 0.0 | 0.0 |
| 3-[(1-Ethylpropyl)amino]-6-isopropyl-2,4-dinitrobenzyl ester of thiocyanic acid | 10.0 | 9.0 | 9.0 | 9.0 | X | 9.0 | 8.0 | 9.0 | 8.0 | 8.0 | X | X | X | X | X | X | X | X |
|  | 2.0 | 9.0 | 9.0 | 9.0 | 8.0 | 3.0 | 8.0 | 8.0 | 7.0 | 8.0 | 0.0 | 0.0 | 1.0 | 5.0 | 0.0 | 0.0 | 5.0 | 0.0 |
|  | 1.0 | 4.5 | 8.0 | 8.0 | 5.5 | 0.0 | 1.5 | 4.5 | 2.5 | 1.5 | 0.0 | 0.0 | 1.0 | 3.5 | 1.5 | 1.5 | 0.0 | 0.0 |
|  | 0.5 | 4.0 | 8.5 | 5.5 | 2.5 | 0.0 | 1.0 | 1.5 | 2.5 | 0.0 | 0.0 | 0.0 | 0.0 | 0.0 | 0.5 | 0.0 | 0.0 | 0.0 |
|  | 0.25 | 3.5 | 8.0 | 3.5 | 1.5 | 0.0 | 0.0 | 0.0 | 0.0 | 0.0 | 0.0 | 0.0 | 0.0 | 0.0 | 0.0 | 0.0 | 0.0 | 0.0 |
|  | 0.125 | 4.0 | 6.5 | 1.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 3-[(1-Ethylpropyl)amino]-6-isopropyl-2,6-dinitrobenzyl alcohol, acetate | 10.0 | 9.0 | 9.0 | 9.0 | X | 8.0 | 8.0 | 9.0 | 8.0 | 7.0 | X | X | X | X | X | X | X | X |
|  | 2.0 | 9.0 | 9.0 | 7.5 | 9.0 | 0.0 | 2.5 | 7.0 | 4.5 | 1.5 | 0.0 | 1.0 | 1.0 | 3.0 | 1.5 | 3.0 | 3.0 | 0.0 |
|  | 1.0 | 6.0 | 9.0 | 7.0 | 6.5 | 0.0 | 1.0 | 5.0 | 2.5 | 1.0 | 0.0 | 0.0 | 0.0 | 0.5 | 0.5 | 1.5 | 0.0 | 0.0 |
|  | 0.5 | 6.0 | 9.0 | 7.0 | 4.0 | 0.0 | 2.5 | 2.5 | 1.0 | 0.0 | 0.0 | 0.0 | 0.0 | 0.0 | 0.0 | 1.5 | 0.0 | 0.0 |
|  | 0.25 | 4.5 | 9.0 | 4.5 | 1.5 | 0.0 | 1.0 | 1.5 | 1.0 | 0.0 | 0.0 | 0.0 | 0.0 | 0.0 | 0.0 | 0.5 | 0.0 | 0.0 |
|  | 0.125 | 4.0 | 8.0 | 1.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| {5-[(1-Ethylpropyl)amino]-4,6-dinitro-o-cumenyl}acetonitrile | 10.0 | 9.0 | 9.0 | 9.0 | X | 9.0 | 8.0 | 9.0 | 9.0 | 9.0 | X | X | X | X | X | X | X | X |
|  | 2.0 | 9.0 | 9.0 | 9.0 | 9.0 | 9.0 | 9.0 | 9.0 | 9.0 | 8.0 | 3.0 | 0.0 | 7.0 | 0.0 | 0.0 | 0.0 | 7.0 | 3.0 |
|  | 1.0 | 6.0 | 9.0 | 9.0 | 8.5 | 5.5 | 8.5 | 9.0 | 8.5 | 7.0 | 0.0 | 0.5 | 3.5 | 2.5 | 1.5 | 1.5 | 2.5 | 0.0 |
|  | 0.5 | 6.0 | 9.0 | 8.5 | 7.0 | 1.0 | 8.5 | 8.5 | 8.0 | 5.5 | 0.0 | 0.0 | 2.5 | 1.5 | 1.5 | 1.5 | 2.5 | 0.0 |

TABLE 1-continued

Preemergence Herbicidal Activity of Compounds of the Invention

| Compound | Rate kg/ha | BA | CR | FO | MJ | MG | MU | PI | SP | VL | BY | CN | CO | RI$_a$ | RI$_b$ | RI$_c$ | SY | WH |
|---|---|---|---|---|---|---|---|---|---|---|---|---|---|---|---|---|---|---|
| {5-[(1-Ethylpropyl)amino]-4,6-dinitro-o-cumenyl}acetaldehyde | 0.25 | 4.0 | 9.0 | 5.5 | 1.5 | 0.0 | 5.5 | 8.0 | 8.0 | 1.5 | 0.0 | 0.0 | 0.0 | 1.5 | 0.0 | 0.0 | 0.5 | 0.0 |
| | 0.125 | 4.0 | 7.5 | 4.0 | 0.0 | 0.0 | 5.5 | 6.0 | 4.5 | 0.0 | 0.0 | 0.0 | 0.0 | 0.0 | 0.0 | 0.0 | 0.0 | 0.0 |
| | 0.063 | 4.0 | 5.5 | 2.5 | 0.0 | 0.0 | 4.5 | 4.5 | 1.5 | 0.0 | 0.0 | 0.0 | 0.0 | 0.0 | 0.0 | 0.0 | 0.0 | 0.0 |
| {5-[(1-Ethylpropyl)amino]-4,6-dinitro-o-cumenyl}acetic acid | 10.0 | 9.0 | 9.0 | 9.0 | X | 8.0 | 9.0 | 9.0 | 8.0 | 7.0 | X | X | X | X | X | X | X | X |
| | 1.0 | 5.0 | 9.0 | 9.0 | 6.0 | 0.0 | 0.0 | 0.0 | 3.0 | 0.0 | 0.0 | 3.0 | 0.0 | 0.0 | 0.0 | 0.0 | 5.0 | 0.0 |
| | 0.5 | 3.0 | 7.0 | 9.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| | 0.25 | 0.0 | 9.0 | 7.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| {5-[(1-Ethylpropyl)amino]-4,6-dinitro-o-cumenyl}acetic acid, methyl ester | 10.0 | 9.0 | 9.0 | 9.0 | X | 8.0 | 9.0 | 9.0 | 8.0 | 8.0 | X | X | X | X | X | X | X | X |
| | 1.0 | 9.0 | 9.0 | 9.0 | 7.0 | 0.0 | 9.0 | 8.0 | 7.0 | 3.0 | 0.0 | 0.0 | 6.0 | 0.0 | 0.0 | 0.0 | 0.0 | 0.0 |
| | 0.5 | 9.0 | 9.0 | 9.0 | 3.0 | 0.0 | 5.0 | 7.0 | 7.0 | 3.0 | 0.0 | 0.0 | 0.0 | 0.0 | 0.0 | 0.0 | 0.0 | 0.0 |
| | 0.25 | 9.0 | 9.0 | 7.0 | 0.0 | 0.0 | 2.0 | 5.0 | 7.0 | 0.0 | 0.0 | 0.0 | 0.0 | 0.0 | 0.0 | 0.0 | 0.0 | 0.0 |
| | 0.125 | 7.0 | 9.0 | 2.0 | 0.0 | 0.0 | 0.0 | 3.0 | 3.0 | 0.0 | 0.0 | 0.0 | 0.0 | 0.0 | 0.0 | 0.0 | 0.0 | 0.0 |
| | 0.063 | 3.0 | 9.0 | 2.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| {5-(sec-Butylamino)-4,6-dinitro-o-tolyl]acetonitrile | 10.0 | 9.0 | 9.0 | 9.0 | X | 8.0 | 8.0 | 8.0 | 8.0 | 2.0 | X | X | X | X | X | X | X | X |
| | 1.0 | 3.0 | 7.0 | 5.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| | 0.5 | 0.0 | 5.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| {5-[(2-Methoxy-1-methylethyl)amino]-4,6-dinitro-o-tolyl}acetonitrile | 10.0 | 9.0 | 9.0 | 9.0 | X | 9.0 | 9.0 | 9.0 | 9.0 | 9.0 | X | X | X | X | X | X | X | X |
| | 1.0 | 9.0 | 9.0 | 9.0 | 9.0 | 0.0 | 8.0 | 7.0 | 8.0 | 3.0 | 0.0 | 0.0 | 0.0 | 0.0 | 0.0 | 0.0 | 0.0 | 0.0 |
| | 0.5 | 9.0 | 9.0 | 5.0 | 8.0 | 0.0 | 7.0 | 7.0 | 0.0 | 0.0 | 0.0 | 0.0 | 0.0 | 0.0 | 0.0 | 0.0 | 0.0 | 0.0 |
| | 0.25 | 9.0 | 3.0 | 0.0 | 0.0 | 0.0 | 0.0 | 3.0 | 3.0 | 0.0 | 0.0 | 0.0 | 0.0 | 0.0 | 0.0 | 0.0 | 0.0 | 0.0 |
| {5-[(1-Methylbutyl)amino]-4,6-dinitro-o-tolyl}acetonitrile | 10.0 | 9.0 | 9.0 | 9.0 | X | 9.0 | 9.0 | 9.0 | 9.0 | 9.0 | X | X | X | X | X | X | X | X |
| | 1.0 | 9.0 | 9.0 | 9.0 | X | 9.0 | 9.0 | 9.0 | 9.0 | 3.0 | X | X | X | X | X | X | X | X |
| | 0.5 | 9.0 | 9.0 | 7.0 | 5.0 | 0.0 | 5.0 | 5.0 | 3.0 | 3.0 | 0.0 | 0.0 | 0.0 | 0.0 | 0.0 | 0.0 | 0.0 | 0.0 |
| | 0.25 | 5.0 | 9.0 | 3.0 | 0.0 | 0.0 | 3.0 | 3.0 | 0.0 | 3.0 | 0.0 | 0.0 | 0.0 | 0.0 | 0.0 | 0.0 | 0.0 | 0.0 |
| {5-[[1-(Hydroxymethyl)propyl]amino]-4,6-dinitro-o-tolyl}acetonitrile | 10.0 | 9.0 | 9.0 | 9.0 | X | 9.0 | 6.0 | 9.0 | 9.0 | X | X | X | X | X | X | X | X | X |
| (4,6-Dinitro-5-propylamino-o-tolyl)acetonitrile | 10.0 | 9.0 | 9.0 | 9.0 | X | 8.0 | 9.0 | 9.0 | 8.0 | 8.0 | X | X | X | X | X | X | X | X |
| | 2.0 | 8.0 | 9.0 | 3.0 | 0.0 | 3.0 | 9.0 | 9.0 | 0.0 | 0.0 | 0.0 | 0.0 | 0.0 | 3.0 | 0.0 | 0.0 | 0.0 | 0.0 |
| | 1.0 | 7.0 | 5.0 | 0.0 | 0.0 | 8.0 | 9.0 | 8.0 | 9.0 | 8.0 | X | X | X | X | X | X | X | X |
| {5-[(1-Ethylbutyl)amino]-4,6-dinitro-o-tolyl}acetonitrile | 10.0 | 9.0 | 9.0 | 9.0 | X | 8.0 | 9.0 | 9.0 | 9.0 | 3.0 | X | X | X | X | X | X | X | X |
| | 1.0 | 5.0 | 9.0 | 5.0 | 3.0 | 0.0 | 5.0 | 8.0 | 3.0 | 8.0 | 0.0 | 3.0 | 0.0 | 0.0 | 0.0 | 0.0 | 0.0 | 0.0 |
| | 0.5 | 5.0 | 9.0 | 0.0 | 0.0 | 0.0 | 0.0 | 6.0 | 3.0 | 0.0 | 0.0 | 0.0 | 0.0 | 0.0 | 0.0 | 0.0 | 0.0 | 0.0 |
| {5-[(3-Chloro-1-ethylpropyl)amino]-4,6-dinitro-o-tolyl}acetonitrile | 10.0 | 9.0 | 9.0 | 9.0 | X | 9.0 | 9.0 | 9.0 | 8.0 | 3.0 | X | X | X | X | X | X | X | X |
| | 1.0 | 9.0 | 9.0 | 7.0 | 9.0 | 8.0 | 8.0 | 6.0 | 3.0 | 0.0 | 0.0 | 0.0 | 0.0 | 0.0 | 0.0 | 0.0 | 0.0 | 0.0 |
| | 0.5 | 8.0 | 9.0 | 3.0 | 8.0 | 0.0 | 0.0 | 7.0 | 8.0 | 3.0 | 0.0 | 0.0 | 0.0 | 0.0 | 0.0 | 0.0 | 5.0 | 0.0 |
| | 0.25 | 5.0 | 9.0 | 0.0 | 0.0 | 0.0 | 3.0 | 5.0 | 3.0 | 0.0 | 0.0 | 0.0 | 0.0 | 0.0 | 0.0 | 0.0 | 5.0 | 0.0 |
| | 0.125 | 3.0 | 7.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| (3-Isopropylamino-2,4-dinitro-6-propylphenyl)acetonitrile | 2.0 | 9.0 | 9.0 | 9.0 | 9.0 | 0.0 | 9.0 | 5.0 | 7.0 | 0.0 | 0.0 | 0.0 | 0.0 | 0.0 | 0.0 | 0.0 | 0.0 | 0.0 |
| | 1.0 | 9.0 | 9.0 | 8.0 | 0.0 | 0.0 | 3.0 | 3.0 | 6.0 | 0.0 | 0.0 | 0.0 | 0.0 | 0.0 | 0.0 | 0.0 | 0.0 | 0.0 |
| | 0.5 | 9.0 | 9.0 | 3.0 | 5.0 | 0.0 | 0.0 | 0.0 | 3.0 | 0.0 | 0.0 | 0.0 | 0.0 | 0.0 | 0.0 | 0.0 | 0.0 | 0.0 |
| | 0.25 | 5.0 | 5.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |

EXAMPLE 19

Evaluation of Postemergence Herbicidal Activity

The postemergence herbicidal activity of the compounds of the present invention is demonstrated by the following tests, wherein crabgrass (3-week-old seedlings) is treated in the presence of seedling and established turf grasses, with test compounds dispersed in aqueous acetone mixtures. In these tests, crabgrass and selected turf grasses are grown in separate cups until the seedlings are, on the average, about 7.5 cm (3") tall. Samples of established turf are taken in the shape of 7–8 cm diameter plugs, and maintained until the grasses are, on the average, 7.5 cm tall. The test compounds are dispersed in 80/20 acetone/water mixtures containing 0.5% TWEEN ®20, polyoxyethylene sorbitan monolaurate surfactant of Atlas Chemical Industries, in sufficient quantity to provide the equivalent of about 0.03 kg to 2.0 kg per hectare of active compound when applied to the plants through a spray nozzle operating at 2.81 kg/cm$^2$ pressure for a predetermined time. After spraying, the plants are placed on greenhouse benches and are cared for in the usual manner, commensurate with conventional greenhouse practices. Four weeks after treatment, the seedling plants and established turf grasses are examined and rated according to the rating system provided in Example 18. The data obtained are reported in Table II below, wherein it can be clearly seen that the compounds of the invention applied postemergence, selectively control crabgrass and selected broad-leaved weeds in the presence of established turf grasses.

Plant Species

Crabgrass (*Digitaria sanguinalis*)
Purslane (*Portulaca oleracea, L.*)
Bentgrass, Colonial (*Agrostis tenuis*)
Bluegrass, Kentucky (*Poa pratensis, L.*)
Fescue, Chewings (Red) (*Festuca rubra commutata*)

TABLE II

Evaluation of the Postemergence Herbicidal Activity of Compounds of the Invention Against Crabgrass and Purslane in the Presence of Turf Grasses

| | | Plant Species | | | | | | |
| | | Crabgrass | | Bent-grass | | Blue-grass | | Fescue |
| | Rate | 3-Week | Purslane | | | | | |
| Compound | kg/ha | Stage | b | a | b | a | b | a | b |
|---|---|---|---|---|---|---|---|---|
| N—(1-Ethylpropyl)-α$^3$- | 2.0 | 9 | 5 | 9 | 3 | X | 5 | 9 | 9 |
| methoxy-2,6-dinitro- | 1.0 | 9 | 5 | 8 | 0 | X | 1 | 7 | 9 |
| 3,4-xylidine | 0.50 | 9 | 5 | 8 | 7 | X | 0 | 7 | 0 |
| | 0.25 | 9 | 2 | 5 | 7 | X | 0 | 0 | 0 |
| | 0.125 | 9 | 2 | 1 | 0 | X | 0 | 0 | 0 |
| | 0.063 | 8 | 1 | 0 | 0 | X | 0 | 0 | 0 |
| | 0.032 | 1 | 0 | 0 | 0 | X | 0 | 0 | 0 |
| N—(1-Ethylpropyl)-7- | 2.0 | 9 | 8 | 9 | 2 | X | 3 | 9 | 9 |
| methoxy-4,6-dinitro- | 1.0 | 9 | 7 | 9 | 2 | X | 1 | 8 | 8 |
| o-cymen-5-amine | 0.50 | 9 | 6 | 9 | 2 | X | 1 | 7 | 7 |
| | 0.25 | 9 | 6 | 7 | 1 | X | 1 | 6 | X |
| | 0.125 | 9 | 5 | 5 | 0 | X | 0 | 3 | 0 |
| | 0.063 | 6 | 5 | 0 | 0 | X | 0 | 0 | 0 |
| | 0.032 | 2 | 5 | 0 | 0 | X | 0 | 0 | 0 |
| 4-Ethyl-N—(1-ethyl- | 2.0 | 9 | 8 | 9 | 8 | X | 3 | 9 | 7 |
| propyl)-α-methoxy-2,6- | 1.0 | 9 | 8 | 9 | 7 | X | 2 | 9 | 7 |
| dinitro-m-toluidine | 0.50 | 9 | 7 | 9 | 9 | X | 1 | 7 | 9 |
| | 0.25 | 9 | 5 | 7 | 1 | X | 1 | 7 | 6 |
| | 0.125 | 9 | 5 | 6 | 0 | X | 0 | 2 | 5 |
| | 0.063 | 9 | 5 | 0 | 0 | X | 0 | 0 | 0 |
| | 0.032 | 4 | 3 | 0 | 0 | X | 0 | 0 | 0 |
| 4-sec-Butyl-N—(1-ethyl- | 2.0 | 9 | 5 | 9 | 3 | X | 0 | 9 | X |
| propyl-α-methoxy-2,6- | 1.0 | 9 | 5 | 9 | 0 | X | 0 | 6 | X |
| dinitro-m-toluidine | 0.50 | 7 | 5 | 6 | 0 | X | 0 | 5 | X |
| | 0.25 | 6 | 2 | 5 | 0 | X | 0 | 0 | X |
| | 0.125 | 0 | 2 | 1 | 0 | X | 0 | 0 | X |
| | 0.063 | 0 | 4 | 0 | 0 | X | 0 | 0 | 0 |
| | 0.032 | 0 | 2 | 0 | 0 | X | 0 | 0 | 0 |
| {5-[(1-Ethylpropyl)- | 2.0 | 9 | 5 | 9 | 2 | X | 0 | 9 | X |
| amino]-4,6-dinitro-o- | 1.0 | 9 | 5 | 8 | 2 | X | 0 | 7 | X |
| tolyl}acetonitrile | 0.50 | 9 | 2 | 3 | 0 | X | 0 | 6 | X |
| | 0.25 | 7 | 2 | 2 | 0 | X | 0 | 1 | 0 |
| | 0.125 | 0 | 2 | 1 | 0 | X | 0 | 0 | 0 |
| | 0.063 | 0 | 2 | 0 | 0 | X | 0 | 0 | 0 |
| | 0.032 | 0 | 0 | 0 | 0 | X | 0 | 0 | 0 |
| {5-[(1-Ethylpropyl)- | 2.0 | 9 | 9 | 9 | 6 | X | 3 | 8 | 9 |
| amino]-4,6-dinitro-o- | 1.0 | 9 | 9 | 9 | 5 | X | 1 | 8 | 8 |
| cumenyl}acetonitrile | 0.50 | 9 | 6 | 8 | 0 | X | 0 | 7 | 0 |
| | 0.25 | 9 | 7 | 4 | 0 | X | 0 | 3 | 0 |
| | 0.125 | 7 | 5 | 2 | 0 | X | 0 | 0 | 0 |
| | 0.063 | 0 | 3 | 0 | 0 | X | 0 | 0 | 0 |
| | 0.032 | 0 | 0 | 0 | 0 | X | 0 | 0 | 0 | a - Seedling turf
b - Established turf

EXAMPLE 20

Evaluation of Postemergence Herbicidal Activity

By the method of Example 19, the postemergence herbicidal activity of a number of compounds is evaluated, except that in these tests both two- and three-week-old crabgrass seedlings are included. Also included in these tests is N-(1-ethylpropyl)-α$^3$-methoxy- 2,6-dinitro-3,4-xylidine, a compound of Example 19 for comparative purposes.

The data obtained are reported in Table III below.

TABLE III

Evaluation of the Postemergence Herbicidal Activity of Compounds of the Invention Against Crabgrass and Purslane in the Presence of Turf Grasses

| | | Plant Species | | | | | | | | |
|---|---|---|---|---|---|---|---|---|---|---|
| | | Crabgrass | | | Bent-grass | | Blue-grass | | Fescue | |
| Compound | Rate kg/ha | 2-Week Stage | 3-Week Stage | Purslane b | a | b | a | b | a | b |
| N—(1-Ethylpropyl)-α³-methoxy-2,6-dinitro-3,4-xylidine | 2.0 | 9 | 9 | 9 | 9 | 8 | 9 | 0 | 7 | X |
| | 1.0 | 9 | 9 | 8 | 7 | 5 | 8 | 0 | 7 | X |
| | 0.50 | 9 | 9 | 7 | 6 | 0 | 8 | 0 | 3 | X |
| | 0.25 | 9 | 8 | 6 | 4 | 0 | 6 | 0 | 0 | X |
| | 0.125 | 9 | 7 | 6 | 0 | 0 | 5 | 0 | 0 | X |
| | 0.063 | 8 | 7 | 5 | 0 | 0 | 0 | 0 | 0 | X |
| | 0.032 | 7 | 0 | 5 | 0 | 0 | 0 | 0 | 0 | X |
| 4-Ethyl-N—isopropyl-α-methoxy-2,6-dinitro-m-toluidine | 2.0 | 9 | 9 | 9 | 8 | 3 | 9 | 0 | 5 | X |
| | 1.0 | 9 | 8 | 8 | 6 | 3 | 8 | 0 | 3 | X |
| | 0.50 | 9 | 7 | 7 | 4 | 0 | 6 | 0 | 0 | X |
| | 0.25 | 7 | 3 | 6 | 0 | 0 | 3 | 0 | 0 | X |
| | 0.125 | 5 | 0 | 6 | 0 | 0 | 5 | 0 | 0 | X |
| | 0.063 | 0 | 0 | 5 | 0 | 0 | 0 | 0 | 0 | X |
| | 0.032 | 0 | 0 | 5 | 0 | 0 | 0 | 0 | 0 | X |
| 4-Ethyl-α-methoxy-N—(1-methylbutyl)-2,6-dinitro-m-toluidine | 2.0 | 9 | 9 | 8 | 9 | 8 | 9 | 0 | 6 | X |
| | 1.0 | 9 | 9 | 9 | 7 | 5 | 9 | 0 | 5 | X |
| | 0.50 | 9 | 9 | 8 | 7 | 3 | 8 | 0 | 3 | X |
| | 0.25 | 8 | 7 | 7 | 5 | 3 | 7 | 0 | 0 | X |
| | 0.125 | 7 | 0 | 7 | 3 | 0 | 6 | 0 | 0 | X |
| | 0.063 | 4 | 0 | 6 | 0 | 0 | 6 | 0 | 0 | 0 |
| | 0.032 | 2 | 0 | 5 | 0 | 0 | 5 | 0 | 0 | 0 |
| N—isopropyl-7-methoxy-4,6-dinitro-o-cymen-5-amine | 2.0 | 9 | 9 | 9 | 9 | 5 | 8 | 0 | 6 | X |
| | 1.0 | 9 | 9 | 8 | 3 | 2 | 8 | 0 | 2 | X |
| | 0.50 | 9 | 8 | 7 | 5 | 0 | 7 | 0 | 0 | X |
| | 0.25 | 8 | 7 | 7 | 0 | 0 | 5 | 0 | 0 | X |
| | 0.125 | 8 | 0 | 5 | 0 | 0 | 0 | 0 | 0 | X |
| | 0.063 | 5 | 0 | 5 | 0 | 0 | 0 | 0 | 0 | X |
| | 0.032 | 3 | 0 | 3 | 0 | 0 | 0 | 0 | 0 | X |
| 7-Methoxy-N—(2-methoxy-1-methylethyl)-4,6-dinitro-o-cymen-5-amine | 2.0 | 9 | 9 | 7 | 9 | 8 | 9 | 7 | 9 | X |
| | 1.0 | 9 | 9 | 5 | 8 | 5 | 9 | 5 | 6 | X |
| | 0.50 | 9 | 6 | 5 | 6 | 0 | 9 | 0 | 3 | X |
| | 0.25 | 9 | 7 | 4 | 7 | 0 | 8 | 0 | 0 | X |
| | 0.125 | 7 | 5 | 3 | 0 | 0 | 4 | 0 | 0 | X |
| | 0.063 | 6 | 2 | 3 | 0 | 0 | 0 | 0 | 0 | X |
| | 0.032 | 2 | 0 | 3 | 0 | 0 | 0 | 0 | 0 | X |
| N—sec-Butyl-7-methoxy-4,6-dinitro-o-cymen-5-amine | 2.0 | 9 | 9 | 8 | 9 | 8 | 9 | 3 | 7 | X |
| | 1.0 | 9 | 9 | 8 | 9 | 4 | 9 | 0 | 6 | X |
| | 0.50 | 9 | 9 | 8 | 8 | 0 | 7 | 0 | 4 | X |
| | 0.25 | 9 | 8 | 7 | 3 | 0 | 7 | 0 | 2 | X |
| | 0.125 | 9 | 7 | 6 | 0 | 0 | 6 | 0 | 0 | X |
| | 0.063 | 8 | 0 | 6 | 0 | 0 | 6 | 0 | 0 | X |
| | 0.032 | 6 | 0 | 4 | 0 | 0 | 3 | 0 | 0 | X |
| N—(1-Ethylbutyl)-7-methoxy-4,6-dinitro-o-cymen-5-amine | 2.0 | 9 | 9 | 9 | 9 | 6 | 9 | X | 7 | X |
| | 1.0 | 9 | 9 | 8 | 9 | 5 | 9 | 3 | 6 | X |
| | 0.50 | 9 | 9 | 8 | 7 | 2 | 8 | 0 | 6 | X |
| | 0.25 | 9 | 7 | 6 | 6 | 0 | 8 | 0 | 2 | X |
| | 0.125 | 8 | 7 | 6 | 5 | 0 | 6 | 0 | 0 | X |
| | 0.063 | 7 | 0 | 6 | 3 | 0 | 5 | 0 | 0 | X |
| | 0.032 | 6 | 0 | 5 | 0 | 0 | 3 | 0 | 0 | X | a- Seedling turf
b - Established turf

We claim:

1. A method for the selective preemergence control of monocotyledonous and dicotyledonous plant species in the presence of graminaceous crops comprising: applying to the soil containing the seeds or seedlings of the plants a herbicidally effective amount of the compound 5-[(1-ethylpropyl)amino]-4,6-dinitro-o-tolyl acetonitrile.

* * * * *